(12) United States Patent
Fritzsch et al.

(10) Patent No.: US 6,383,470 B1
(45) Date of Patent: *May 7, 2002

(54) MICROPARTICLE PREPARATIONS MADE OF BIODEGRADABLE COPOLYMERS

(76) Inventors: Thomas Fritzsch, Elisenstr. 2, 12169 Berlin; Dieter Heldmann, Krefelder Str. 3; Werner Weitschies, Jagowstr. 20, both of 10555 Berlin, all of (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 64 days.

(21) Appl. No.: 08/897,319

(22) Filed: Jul. 21, 1997

Related U.S. Application Data

(63) Continuation of application No. 08/406,882, filed as application No. PCT/EP93/02422 on Sep. 8, 1993, now abandoned.

(30) Foreign Application Priority Data

Sep. 26, 1992 (DE) .......................... 42 32 755

(51) Int. Cl.$^7$ .............................................. A61K 49/04
(52) U.S. Cl. ...................................... 424/9.42; 424/9.4
(58) Field of Search ................... 424/426, 489, 424/450, 464, 9.1, 9.4, 9.3, 9.52; 514/61

(56) References Cited

U.S. PATENT DOCUMENTS

| 4,267,234 A | 5/1981 | Rembaum ................... 428/403 |
| 4,276,885 A | 7/1981 | Tickner et al. ............... 128/660 |
| 4,349,530 A | 9/1982 | Royer ........................ 424/489 |
| 4,438,239 A | 3/1984 | Rembaum et al. .......... 525/54.1 |
| 4,677,138 A | 6/1987 | Margel ........................ 522/178 |
| 4,678,814 A | 7/1987 | Rembaum ................... 522/175 |
| 4,718,433 A | 1/1988 | Feinstein .................... 128/660 |
| 4,732,811 A | 3/1988 | Margel ........................ 428/403 |
| 4,783,336 A | 11/1988 | Margel et al. ............... 424/462 |
| 4,937,081 A | 6/1990 | Kagotani .................... 424/498 |
| 4,997,454 A | 3/1991 | Violante et al. .......... 23/305 A |
| 5,019,400 A | 5/1991 | Gombotz et al. ........... 424/497 |
| 5,393,524 A | 2/1995 | Quay ............................. 424/9 |
| 5,409,688 A | 4/1995 | Quay ............................. 424/9 |
| 5,470,843 A | * 11/1995 | Stahl et al. ................... 514/61 |
| 5,501,863 A | 3/1996 | Rössling et al. |
| 5,618,514 A | 4/1997 | Schröder et al. |
| 5,665,383 A | * 9/1997 | Grinstaff .................... 424/450 |
| 5,711,933 A | * 1/1998 | Bichon et al. ............. 424/9.52 |

FOREIGN PATENT DOCUMENTS

| EP | 0 324 938 | 7/1989 |
| EP | 0 327 490 | 8/1989 |
| EP | 0 441 468 | 8/1991 |
| EP | 0 458 745 | 11/1991 |
| EP | 556 917 | 8/1993 |
| EP | 458 079 | 7/1994 |
| WO | 84/02838 | 8/1984 |
| WO | WO89/06978 | 8/1989 |
| WO | 92/04392 | 3/1992 |
| WO | 92/17212 | 10/1992 |
| WO | 92 17213 | 10/1992 |
| WO | 93/17718 | 9/1993 |

OTHER PUBLICATIONS

*British Medical Journal*, vol. 1, No. 5952, pp. 247–249 (Feb. 1975).
PCT Search Report dated Jun. 12, 1989, EP 91 25 0038.

* cited by examiner

Primary Examiner—Thurman K. Page
Assistant Examiner—Robert Joynes

(57) ABSTRACT

The invention relates to microparticle preparations made of biodegradable copolymers for use in treatment and diagnosis, especially ultrasonic diagnosis, as well as a process for their production.

21 Claims, No Drawings

MICROPARTICLE PREPARATIONS MADE OF BIODEGRADABLE COPOLYMERS

This application is a continuation of application Ser. No. 08/406,882, filed Apr. 27, 1995, now abandoned, which is a 371 of PCT/EP93/02422 filed Sep. 8, 1993.

The invention relates to the object characterized in the claims, i.e., microparticles produced from biopolymers, monomers capable of polymerization, active ingredients and/or diagnostically detectable components, a process for their production as well as their use in diagnosis and treatment, especially as contrast media in ultrasonic diagnosis.

It is known that particles, whose diameter is smaller or in the range of the size of red blood cells, can circulate within the circulatory system after injection in the circulatory pathway. Pharmaceutical preparations of such microparticles are thus suitable as vehicle systems injectable in the circulatory system for active ingredients or diagnostic agents in medicine. As vehicle materials, in principle all biodegradable, compatible and non-water-soluble substances are suitable. So far, above all fats, waxes, lipids (e.g., soybean lecithin), denatured biopolymers (e.g., albumin, gelatin) and synthetically biodegradable polymers (e.g., polylactic acid, polyhydroxybutyric acid, polyalkylcyanoacrylates, poly-L-lysine) are described.

There is a difference in how quickly and in the numbers in which the microparticles circulating in the circulatory pathway are recognized, as a function of their physical and chemical properties, by the cells of the monocytic phagocytizing system (MPS) and taken up (mainly in the liver, lung and spleen). The particle charge, the particle size, the properties (molecular weight, amphiphilia) on the particle surface of adsorbed substances, as well as the affinity of the particle surface for blood components such as fibronectin, albumin, etc. are considered as essential factors, which determine the kinetics of the absorption of the microparticles by the cells of the MPS. By specific variation of the physicochemical surface properties of microparticles, the kinetics of the phagocytosis can be influenced by the cells of the MPS and the extent of the concentration of the particles within the corresponding organs (i.a., liver, lung, spleen, bone marrow) (passive targeting). A specific concentration of microparticles in target tissues or body structures, which are not among the organs of the RES, is in this way not possible. It can rather be achieved only by the combination of the microparticles with substances which have site-specific, structure-specific or tissue-specific binding properties (homing devices). But the particles previously described for use in ultrasonic diagnosis are suitable only insufficiently as preparations suitable for the combination with homing devices.

Thus, it has to be accepted in the case of the contrast media described in EP 0 458 079 and DE 38 03 972 that they can be produced only with the help of expensive processes, which make necessary the use of organic solvents, whose use is harmful for reasons of protection of the environment and work place safety. In addition, before using the preparations, there has to be assurance that the used organic solvents are no longer contained in the product to be used pharmaceutically. Moreover, surface-active adjuvants (e.g., surfactants) are necessary for the production, which are frequently considered as harmful in the case of injection preparations. Further, a control of the concentration behavior in various organs is not controllable in the case of these particles, a linkage of the particles of DE 38 03 972 with selectively accumulating compounds (so-called homing devices, such as, e.g., monoclonal antibodies) is not possible.

The microparticles made of polymerized aldehydes described in DE 40 04 430 are also not suitable as vehicles for substance-specific or structure-specific substances because of the unclear biodegradability. Another drawback is that also in this case surface-active adjuvants are necessary for the production of the particles.

The microparticles made of proteins, especially of albumin, described in EP 0 224 934 exhibit an only very low in vitro and in vivo stability.

It was therefore the object of the invention to provide microparticle preparations especially for use in ultrasonic diagnosis, which get by without the use of physiologically harmful solvents or adjuvants (e.g., surfactants), are easily producible and biodegradable, which either contain substances with site-specific, structure-specific or tissue-specific binding properties in the wall material or can be linked covalently with such and which exhibit a sufficient in vitro and in vivo stability.

According to the invention, this object is achieved by microparticles whose shell is formed from the combination of biopolymers—preferably polypeptides (also glycosylated)—and synthetic material polymerized during the production.

Therefore, microparticles made of a copolymer of at least one synthetic polymer and at least one biopolymer are an object of the invention, and polypeptides, preferably natural ones, or produced synthetically or partially synthetically or obtained by genetic engineering as biopolymers, such as, e.g., albumin, collagen decomposition products, gelatin, fibrinogen, fibronectin, polygeline, oxypolygelatin, their decomposition products as well as poly-L-lysine are suitable. The biopolymers can also be glycosylated. As polymerizable monomers, preferably alkylcyanoacrylates, acrylic acid, acrylamide, acrylic acid chloride and acrylic acid glycide ester are suitable.

The microparticles according to the invention are suitable in the production in gas-saturated solution by the inclusion of the gas, especially as a contrast medium for ultrasonic studies. They act as highly effective scatter elements in the ultrasonic field because of the contained gas. In addition, they can be excited by diagnostic ultrasound to radiate independent signals, which can be evaluated, e.g., with the help of the color Doppler technology.

As gases, air, nitrogen, carbon dioxide, oxygen, helium, neon, argon, krypton or their mixtures are suitable. The charge with the corresponding gas or gas mixture takes place by production of the particles in an aqueous solution saturated with the respective gas or gas mixture.

The microparticles can also (optionally in addition) contain other substances, detectable with the help of medicinally-diagnostic processes, such as magnetic resonance tomography, magnetic resonance spectroscopy, scintigraphy or highly sensitive magnetic field measurements with suitable magnetometers (biomagnetism), both microencapsulated and in the wall material and (optionally with the help of suitable substances, such as, e.g., chelating agents) coupled to the wall material. Thus, it is possible, e.g., in using radioactive isotopes, to use the microparticles according to the invention in scintigraphy. Likewise, its use as contrast medium in magnetic resonance tomography, magnetic resonance spectroscopy or in measurements of the magnetic field is possible by the microencapsulation or incorporation in the wall material of suitable para-, superpara-, ferri- or ferromagnetic substances.

Surprisingly, it has been found that in the production of the particles according to the invention (in maintaining sufficient concentrations of biopolymers), the addition of surface-active substances, such as, e.g., surfactants, is not necessary. This represents a decisive advantage in comparison with the previously known production process for microparticles based on synthetic polymers, since the surfactants usually necessary for reducing the interfacial tension and for preventing the particle aggregation are considered as physiologically harmful and therefore are to be removed again from the preparations before the use in the organism up to compatible residue contents.

As a further advantage of the microparticle preparations according to the invention, the varied particle properties that can be matched to the respective use can be mentioned, which are easily controllable by variation of various production parameters. Thus, the pharmacokinetic parameters of the microparticle preparations, (organ distribution, retention period in the circulatory pathway) can be influenced by the selection of the respectively used biopolymers or by changes of the functional groups of the biopolymer (e.g., by acylation with dicarboxylic anhydrides, such as succinic acid, diglycolic acid, glutaric acid, maleic acid or fumaric acid anhydride or by acetylation with monocarboxylic anhydrides, such as acetic anhydride or propionic acid anhydride).

Further, the content of the biopolymer in the wall material can be varied in a wide scope, by which it is possible to influence the period of the biodegradation of the capsule material in vivo and to match it to the desired use. This content can be controlled directly by the portion of the biopolymer in the production solution. Thus, for example, the wall material consists of microparticles according to the invention, made of 55% (M/M) biopolymers, produced according to example 1 from an autoclaved aqueous solution containing 1% (V/V) butylcyanoacrylic acid and 5% gelatin, while with the same use of butylcyanoacrylate with microparticles produced in 2.5% aqueous autoclaved gelatin solution, the wall material consists of 35% (M/M) biopolymers, with microparticles produced in 7.5% aqueous autoclaved gelatin solution, the wall material consists of 65% (M/M) biopolymers.

Surprisingly, the microparticles according to the invention can be freeze-dried without adding other adjuvants such as lactose, mannitol or sorbitol, as they are usually used as skeleton formers for freeze-drying. These skeleton formers are responsible, after drying, for the mechanical destruction of a considerable part of the microcapsules, which then is no longer usable for the imaging. In contrast to this, in the case of the microparticles according to the invention, the biopolymer of the wall material used in excess is used as a skeleton former, by which surprisingly the ratio of intact to destroyed microcapsules is drastically improved. Because of this more favorable ratio, the dose necessary for imaging can clearly be reduced.

But the microparticles according to the invention can also—optionally in addition—contain incorporated pharmaceutical active ingredients, by, e.g., the opacifying agent (in the case of contrast media for ultrasonic studies, a gas or gas mixture is involved here) and one or more active ingredients in the particles being microencapsulated. Preferably, the active ingredients can also be incorporated in the wall material with the methods described for the site-specific, structure-specific or tissue-specific substances. If the active ingredients are biopolymers, they can also partially form the wall material themselves, by being used in the production either exclusively or in a mixture with other suitable biopolymers (e.g., gelatin, albumin, fibronectin, poly-L-lysine) as initial material for microparticle preparation with the addition of a polymerizable monomer or oligomer. The special advantage of coupling active ingredients to the biopolymer portion of the capsule material lies in the fact that active ingredients, which, e.g., are bound by peptide bonds to the biopolymer portion of the capsule material, can be released by enzymatic decomposition in vivo.

The microparticles according to the invention are used especially to detect or to treat thromboses and atherosclerotic changes. In this case, the use of antibodies or antibody fragments against fibrin, fibrin-bonding plasma proteins or their partial structures, tissue plasminogen activators or partial structures of them (e.g., type I-homology and doughnut sequences), protein components of lipoproteins (also partial structures) as homing devices can be considered as especially advantageous.

Other fields of use for the microparticles according to the invention can be, e.g., also the diagnosis or the treatment of hormonal functions (in this case, the use of peptide hormones or their modified products with the capability for receptor bonding as homing devices is to be considered as especially advantageous), or the diagnosis or treatment of lesions of vascular endothelia (in this case, either the use of antibodies or antibody fragments against substances of the integrin group, especially the selectins such as, e.g., LAM-1, ELAM-1 and GMP140, or the use of receptors or their bond-imparting fragments for substances of the integrin group, especially the selectins such as, e.g., LAM-1, ELAM-1 and GMP-140, as homing devices is to be considered as especially advantageous). Moreover, the microparticles according to the invention can also be used for diagnosis or treatment of tumors, by antibodies or antibody mixtures being used as homing devices against surface antigens of tumors.

The production of microparticles according to the invention takes place by the polymerization of a suitable reactive monomer or oligomer (e.g., cyanoacrylic acid butyl ester, cyanoacrylic acid isobutyl ester, cyanoacrylic acid isopropyl ester, cyanoacrylic acid propyl ester, cyanoacrylic acid isohexyl ester, cyanoacrylic acid hexyl ester, cyanoacrylic acid methyl ester, acrylic acid, acrylamide, acrylic acid glycide ester, acrylic acid chloride) in a concentration relative to the total volume of the production solution of 0.01–10% (m/V) (preferably 0.1–10%) under suitable conditions (e.g., by selection of the pH, by adding radicals, and by UV irradiation) with dispersion in aqueous phase, which contains a biopolymer, e.g., albumin, gelatin, oxypolygelatin, polygeline, fibronectin, poly-L-lysine dissolved in a concentration of 0.5–20% (m/V) (preferably 1%–15% (m/V)). By using collagen decomposition products, such as, e.g., gelatin, polygeline or oxypolygelatin, it is often advantageous to autoclave the solutions before the microparticle production. After completion of the polymerization, the resulting microparticles are separated depending on density and particle size by one-time or repeated centrifuging, filtration or flotation, optionally further purified by dialysis and suspended in a physiologically compatible suspending agent (preferably water for injection purposes) until the desired concentration. The suspensions can be isotonized by the addition of suitable water-soluble substances, such as, e.g., glucose, mannitol, sorbitol, common salt, galactose, lactose, fructose, trehalose.

The size distribution of the microparticles developing in the production can be controlled within wide ranges by the type of stirring device used and the number of revolutions.

The production of gas-filled microparticles takes place by the reaction being performed in a solution saturated with the desired gas. In this connection, the density of the resulting microparticles, i.e. the ratio between wall material and gas portion, can be controlled both by the stirring conditions and especially by the portion of biopolymers during the production process.

If microparticles are to be obtained, in which the core consists of the same material as the shell, attention must be paid in the production that by the selection of a suitable stirring device and a suitable stirring speed, a foaming of the reaction solution is avoided.

The required ability for combination with site-specific, structure-specific or tissue-specific substances, which are to assure an additional concentration of the microparticles in target fields outside the organs of the RES (homing devices), takes place either by the coupling of the substances to the polypeptides co-forming the shell material, performed before the microparticle preparation or afterwards, with known methods of biochemistry for coupling amino acids (e.g., W. König, R. Geiger: Eine neue Methode zur Synthese von Peptiden: Aktivierung der Carboxylgruppe mit Dicyclohexylcarbodiimid unter Zusatz von 1-Hydroxybenzotriazolen [A New Method to Synthesize Peptides: Activation of the Carboxyl Group with Dicyclohexylcarbodiimide while Adding 1-Hydroxy-benzotriazoles], Chem. Ber. 103, 788–798 (1970)), or in that the microparticles are produced in an aqueous solution. of the site-specific, structure-specific or tissue-specific substance, if the latter represents a polypeptide, so that the substance is used directly as a component of the shell material.

As site-specific, structure-specific or tissue-specific substances that can be coupled to the microparticles or co-forming the shell material, preferably antibodies, conjugated antibodies, hormones (especially peptide hormones), transferrin, fibronectin, heparin, transcobalamin, epidermal growth factors, lipoproteins, plasma proteins as well as their specificity-imparting partial structures and oligopeptides such as RGD, RGDS, RGDV and RGDT are suitable.

As chelating ligands that can be coupled to the microparticles, diethylenetriaminepentaacetic acid or its derivatives are suitable. The linkage of these ligands with the particles takes place in a way known in the art [Hanatowich et al., Science 220 (1983) 613]. Then, the particles are reacted with the desired metal ions to the respective particle-fixed metal complex.

The selection of the used metal ion depends on the desired area of use. In the field of NMR diagnosis, paramagnetic metal ions, preferred according to the invention, of the elements of atomic numbers 21–29 and 57–70, especially gadolinium(III) ions, are used. For the use in scintigraphy, suitable emitters of radioactive radiation, preferably $^{111}$In or $^{99m}$Tc, $^{123}$I and $^{131}$I are used.

The finished microparticle suspensions can be used directly for the respectively predetermined use, but it has proven advantageous to improve the storage stability, to freeze and then to freeze-dry the suspensions while adding skeleton formers (such as, e.g., trehalose, polyvinylpyrrolidone, lactose, mannitol, sorbitol, glycine), which also can be used to set the tonicity. It has proven especially advantageous to use the biopolymer used in excess itself as skeleton former. In both cases, it is suitable to move the suspensions during the freezing to prevent uneven particle distributions in the frozen material by sedimentation or flotation. The production of ready-to-use, injectable suspensions from the freeze-dried preparations takes place by resuspending the lyophilizate in a pharmaceutically acceptable suspension medium such as, e.g., water p.i., aqueous solutions of one or more inorganic salts such as physiological electrolyte solutions, aqueous solutions of monosaccharides or disaccharides such as glucose or lactose, sugar alcohols such as mannitol, but preferably in water suitable for injection purposes. The total concentration of the optionally dissolved substances is 0–20% by weight.

The concentration of the ready-to-use contrast medium can be set in the range of 0.01 to 20 mg, preferably 0.5 to 6 mg of particles/ml of suspension medium. The injected dose depends on the respective use; in ultrasonic diagnostic studies in the study of vessels, it lies in the range of 1 to 500 µg, preferably between 10 and 100 µg of particles/kg of body weight, in the study of liver and spleen by color Doppler sonography in the range of 50 to 1000, preferably between 200 and 600 µg/kg of body weight. The invention is explained by the following examples:

EXAMPLE 1

In 300 ml of distilled water, 15 g of gelatin (300 bloom) is dissolved and adjusted to pH 3.0 with hydrochloric acid. The solution is autoclaved for 30 minutes at 121° C. After cooling to room temperature, the pH of the solution is corrected to pH 5.0 (with sodium hydroxide solution) and stirred in a 2000 ml beaker with a quick-running stirrer at 10000 rpm. 3 ml of cyanoacrylic acid butyl ester is slowly (10 minutes) instilled in the solution with stirring. Stirring of the resulting microparticles is continued for 60 minutes. Then, the suspension is floated in a separatory funnel for 2 days. The subnatant is drained and the supernatant is supplemented with distilled water to 100 ml. The suspension contains gas-filled, sound-active microparticles in a size of about 0.1–8 µm, and by additional flotation or filtration, if necessary, the particle sizes can be further concentrated (e.g., to.0.5–3 µm). The capsule wall of the microparticle item consists to about 55% (M/M) of polypeptides and to about 45% (M/M) of polycyanoacrylic acid butyl ester. The particles can be dispersed in water without the addition of surface-active adjuvants. They do not tend toward aggregation. By adding a suitable adjuvant (e.g., glucose, sodium chloride, mannitol, lactose, galactose), the suspension can be isotonized.

The suspension can be freeze-dried, if necessary, to increase the storage stability without losing its suitability as a contrast medium for ultrasonic studies, preferably after adding a cryoprotector, such as, e.g., lactose, polyvinylpyrrolidone, mannitol, glycine.

EXAMPLE 2

500 mg of poly-L-lysine (MG 5000) is dissolved in 20 ml of distilled water and adjusted to pH 4.5 with phosphate buffer. 100 mg of acrylic acid glycide ester is added, the mixture is stirred with a quick-running stirrer under cooling at 20° C. 10 mg of ammonium peroxydisulfate and 0.1 ml of N,N,N',N'-tetramethylenediamine are added. It is stirred for another 90 minutes. The resulting gas-filled microparticles are separated by flotation. The particle size of the microparticles is between 0.2 and 6 µm.

EXAMPLE 3

7.5 g of polygeline is dissolved in 200 ml of water for injection purposes. The solution is adjusted to pH 3.0 with phosphoric acid and supplemented with water for injection purposes to 300 ml. The solution is filtered through a 0.22 µm filter for sterilization by filtration and stirred with a quick-rotating dissolver at 6000 rpm. With stirring, a mixture of 1.5 ml of cyanoacrylic acid isopropyl ester and 1.5 ml of cyanoacrylic acid butyl ester is slowly instilled. Stirring is continued for 120 minutes. The resulting suspension is floated for three days in a separatory funnel. The further course of action corresponds to example 1. The resulting microparticles contain gas. They are suitable as contrast media for ultrasonic studies. Their wall material consists to about 22% (M/M) of biopolymer, to about 40% (M/M) of polycyanoacrylic acid butyl ester and to about 38% (M/M) of polycyanoacrylic acid isopropyl ester. They can be dispersed in water without adding surface-active adjuvants without in this connection aggregating. Their particle size is about 0.2–6 μm.

EXAMPLE 4

10 g of human serum albumin is dissolved in 200 ml of water for injection purposes. The solution is adjusted to pH 4.0 with hydrochloric acid and supplemented with water for injection purposes to 300 ml. The solution is filtered through a 0.22 μm filter for sterilization by filtration and stirred with a quick-rotating dissolver at 10000 rpm. With stirring, 2 ml of cyanoacrylic acid isopropyl ester is slowly instilled. Stirring is continued for 60 minutes. The resulting suspension is floated for three days in a separatory funnel. The further course of action corresponds to example 1. The resulting microparticles contain gas. They are suitable as contrast media for ultrasonic studies. Their wall material consists to about 30% (M/M) of human serum albumin and to about 70% (M/M) of polycyanoacrylic acid isopropyl ester. They can be dispersed in water without adding surface-active adjuvants without in this connection aggregating. Their particle size is on the average about 0.2–3 μm.

EXAMPLE 5

250 ml of oxypolygelatin solution is adjusted to pH 2.5 with hydrochloric acid and supplemented with water for injection purposes to 300 ml. The solution is filtered through a 0.22 μm filter for sterilization by filtration and stirred with a quick-rotating rotor-stator-stirrer at 8000 rpm. With stirring, 3 ml of cyanoacrylic acid butyl ester is slowly instilled. Stirring is continued for 90 minutes. The resulting suspension is floated for three days in a separatory funnel. The further course of action corresponds to example 1. The resulting microparticles contain gas. They are suitable as contrast media for ultrasonic studies. Their wall material consists to about 25% (M/M) of oxypolygelatin and to about 75% (M/M) of polycyanoacrylic acid butyl ester. They can be dispersed in water without adding surface-active adjuvants without in this connection aggregating. Their particle size is about 0.2–4 μm.

EXAMPLE 6

500 mg of fibronectin is dissolved in 5 ml of distilled water and adjusted to pH 3.5 with hydrochloric acid. The solution is filtered through a 0.22 μm filter for sterilization by filtration and stirred with a quick-rotating rotor-stator-stirrer in a cooled 15 ml vessel (15° C.) at 8000 rpm. With stirring, 0.3 ml of cyanoacrylic acid butyl ester is slowly instilled. Stirring is continued for 90 minutes. The resulting suspension is floated for three days in a separatory funnel. The supernatant is suspended in 2 ml of water for injection purposes, which contains 100 mg of mannitol. The suspension is frozen at −50° C. with shaking and freeze-dried. Before use, the microparticles are redispersed with 2 ml of water for injection purposes. The particle size of the microparticles is on the average 0.8 μm. They are suitable as contrast media for ultrasonic studies. The wall material of the microparticles consists to about 35% (M/M) of fibronectin and to about 65% (M/M) of polycyanoacrylic acid butyl ester.

EXAMPLE 7

100 mg of an antibody against fibrin is dissolved in 4 ml of phosphate buffer (pH 4.5). The solution is filtered through a 0.22 μm filter for sterilization by filtration and stirred in a double-walled stirrer vessel (10 ml capacity) with a quick-rotating dissolver-stirrer under cooling at 6000 rpm. During the stirring, 0.2 ml of cyanoacrylic acid butyl ester is slowly instilled. Stirring is continued for 60 minutes. The resulting suspension is floated for two days in a separatory funnel. The subnatant is drained, the supernatant is mixed with 200 mg of lactose and 2 ml of water for injection purposes. The suspension is frozen at −40° C. with shaking in a cold bath and then freeze-dried. Before use, the microparticles are resuspended with 2 ml of water for injection purposes. They are gas-filled and suitable as contrast media for ultrasonic studies. Their particle size is about 1 μm on the average. The wall material of the microparticles consists to about 20% (M/M) of the antibody and to about 80% (M/M) of polycyanoacrylic acid butyl ester.

EXAMPLE 8

15 g of polygeline is dissolved in 50 ml of water for injection purposes, 2 N sodium hydroxide solution is added drop by drop under pH control. A total of 2 g of diglycolic acid anhydride is added gradually, and the pH is kept between 7.5 and 8.0. After completion of the reaction, the excess diglycolic acid is removed from the solution by repeated ultrafiltration (exclusion limit MG 1000). The acylated polygeline solution is supplemented with water for injection purposes to 300 ml and filtered through a 0.22 μm filter. 3 ml of cyanoacrylic acid butyl ester is slowly added with stirring at 10000 rpm. After completion of the addition, stirring is continued for 60 minutes. The resulting gas-filled microparticles are separated by centrifuging at 1500 rpm (30 minutes) and taken up in 50 ml of water for injection purposes. They can be dispersed in water without adding surface-active adjuvants without aggregating. Their particle size is approximately 0.1–6 μm. The wall material of the microparticles consists to about 45% (M/M) of acylated polygeline and to about 55% (M/M) of polycyanoacrylic acid butyl ester.

EXAMPLE 9

20 ml of the gas-containing microparticles produced according to example 3 is taken up in 20 ml of phosphate buffer of pH 4.5. The suspension is stirred at 4° C. (100 rpm) and 25 mg of (3-dimethylaminopropyl)-N'-ethylcarbodiimide-HCl is added to the mixture. After 60 minutes, 25 mg of fibronectin, which was previously dissolved in 10 ml of phosphate buffer, is added to the microparticle suspension. It is stirred for 60 minutes at 4° C. and for another 120 minutes at room temperature. Then, the suspension is dialyzed three times against phosphate buffer of pH 4.5 (exclusion limit MG 1000) and floated for two days in a separatory funnel. The supernatant is taken up in 20 ml of water for injection purposes, mixed with 5% polyvinylpyrrolidone (m/V), frozen at −40° C. with shaking and freeze-dried.

EXAMPLE 10

The lyophilizate of example 9 is resuspended with 20 ml of 5% glucose solution. 0.1 ml of it is added to 10 ml of PBS solution of 37° C., which contains a freshly produced fibrin clot (diameter 1 mm). After 10 minutes of incubation with shaking in a water bath, the clot is removed, washed five times with 10 ml of PBS (pH 7.4) each and then sonographically studied. In the color Doppler, signals of clinging microparticles can be clearly detected. The procedure is analogous with the particles of example 3 (without the reaction with fibronectin shown in example 9). In the sonographic study of the clots, no clinging microparticles can be detected (also in the color Doppler).

EXAMPLE 11

5 ml of the gas-containing microparticles produced according to example 3 is taken up in 5 ml of phosphate buffer of pH 4.5. The suspension is stirred at 4° C. (100 rpm), and 10 mg of (3-dimethylaminopropyl)-N'-ethylcarbodiimide-HCl is added to the mixture. After five minutes, 2.5 mg of an antibody against fibrin (No. 0541 clone E8, Immunotech, Marseilles, France), which was previously dissolved in 1 ml of phosphate buffer, is added to the microparticle suspension. It is stirred for 60 minutes at 4° C. and for another 120 minutes at room temperature. Then, the suspension is dialyzed three times against phosphate buffer of pH 4.5 (exclusion limit MG 1000) and floated for two days in a separatory funnel. The supernatant is taken up in 2 ml of water for injection purposes, mixed with 5% polyvinylpyrrolidone (m/V), frozen at −40° C. with shaking and freeze-dried.

EXAMPLE 12

The lyophilizate of example 11 is resuspended with 2 ml of 5% glucose solution. 0.1 ml of it is added to 10 ml of PBS solution of 37° C., which contains a freshly produced fibrin clot (diameter 1 mm). After 10 minutes of incubation with shaking in a water bath, the clot is removed, washed five times with 10 ml of PBS (pH 7.4) each and then sonographically studied. In the color Doppler, signals of clinging microparticles can be clearly detected. With the particles of example 3 (without the reaction with the antibody against fibrin shown in example 11), the procedure is analogous. In the sonographic study of the clots, no clinging microparticles can be detected (also in the color Doppler).

EXAMPLE 13

0.1 ml of the resuspended particles of example 6 is examined for their fibrin bond in an experimental set-up analogous to example 11. In the sonographic study, microparticles bound to the clot can be clearly detected.

EXAMPLE 14

0.1 ml of the resuspended particles of example 7 is examined for their fibrin bond in an experimental set-up analogous to example 11. In the sonographic study, microparticles bound to the clot can be clearly detected.

EXAMPLE 15

10 ml of the microparticles produced according to example 8 is taken up in 10 ml of phosphate buffer of pH 4.5, and 20 mg of 1-hydroxybenzotriazole is added. After cooling to 4° C., it is stirred (100 rpm), and 10 mg of (3-dimethylaminopropyl)-N'ethylcarbodiimide-HCl is added. Stirring is continued for 60 minutes at 4° C. Then, it is stirred for another 60 minutes at room temperature. 10 mg of pancreozymin, which was previously dissolved in 5 ml of phosphate buffer, is added to the suspension at room temperature. It is stirred for 120 minutes at room temperature. Then, the suspension is dialyzed five times against phosphate buffer of pH 4.5 (exclusion limit MG 1000) and floated for two days in a separatory funnel. The supernatant is taken up in 10 ml of water for injection purposes, mixed with 5% polyvinylpyrrolidone (m/V), frozen at −40° C. with shaking and then freeze-dried.

EXAMPLE 16

The lyophilizate of example 15 is resuspended with 10 ml of water for injection purposes. 0.1 ml of the suspension is injected in the caudal vein of a rat. After 10 minutes, the pancreas is removed and sonographically studied in a water bath. In the color Doppler, ultrasonic signals of the microparticles can be detected.

EXAMPLE 17

5 ml of the gas-containing microparticles produced according to example 3 is taken up in 5 ml of phosphate buffer of pH 4.5. The suspension is stirred at 4° C. (100 rpm), and 10 mg of (3-dimethylaminopropyl)-N'-ethylcarbodiimide-HCl is added to the mixture. After five minutes, 5 mg of tPA, which was previously dissolved in 1 ml of phosphate buffer, is added to the microparticle suspension. stirring is continued for 24 hours at 4° C. Then, the suspension is dialyzed three times against phosphate buffer of pH 4.5 (exclusion limit MG 1000) and floated for two days in a separatory funnel. The supernatant is taken up in 2 ml of water for injection purposes.

EXAMPLE 18

Two fibrin clots (weight about 50 mg each) are produced, which are added to 20 ml of plasma. 0.05 ml of the particle suspension produced according to example 17 is added to the clots. After 10 minutes, the clots are removed from the plasma, in the sonographic study, signals of clinging microparticles appear in the color Doppler.

EXAMPLE 19

0.6 g of gelatin is dissolved in 20 ml of an aqueous suspension of magnetite particles (about 20 mmol of iron/ml, diameter of the particles about 20 nm). The solution is adjusted to pH 3 with hydrochloric acid. With stirring (3000 rpm), 0.2 ml of cyanoacrylic acid isobutyl ester is slowly added. After completion of the addition, stirring is continued for 90 minutes. The suspension is centrifuged (2000 rpm, 60 minutes). The supernatant is discarded, the subnatant is taken up in 10 ml of PBS of pH 7.4 (10 mmol). The suspension is cooled to 4° C. and with stirring (100 rpm), 10 mg of (3-dimethylaminopropyl)-N'-ethylcarbodiimide-HCl is added. Stirring is continued for 60 minutes at 4° C. Then, 5 mg of an antibody against fibrin (no. 0541 clone E8, Immunotech, Marseilles, France) is added. Stirring is continued for 60 minutes at 4° C. and then for 120 minutes at room temperature. The suspension is ultrafiltered (exclusion limit MG 5000) five times against PBS of pH 7.4 (10 mmol). Then, the suspension is centrifuged (2000 rpm, 60 minutes). The subnatant is taken up in 5 ml of water for injection purposes, which contains 5% mannitol (m/V) and is filtered through a 5 µm membrane filter. The filtrate is frozen at −40° C. and then freeze-dried.

EXAMPLE 20

15 g of gelatin (300 bloom) is dissolved at 80° C. in 150 ml of water for injection purposes. After the cooling, the solution is adjusted to pH 2.5 with 0.1 N HCl and supplemented with water for injection purposes to 300 ml. The solution is autoclaved (process A 121, Deutsches Arzneibuch [German Pharmacopoeia] 9 th Edition). The pH of the autoclaved solution is controlled and if necessary corrected to pH 2.5. 3 ml of cyanoacrylic acid isobutyl ester is added to the solution with stirring. Stirring is continued for 90 minutes. The resulting microparticle suspension is centrifuged at 1000 rpm for 60 minutes, the supernatant is taken up in 50 ml of water for injection purposes and again centrifuged at 1000 rpm for 60 minutes. This is repeated a total of 5 times. The supernatant of the final centrifuging is taken up in 50 ml of PBS (pH 7.0) and added with stirring to 0.1 mg of solid diethylenetriaminepentaacetic acid dianhydride (cf.: Hnatowich et al. (1983) Science 220: 613). It is stirred for 5 minutes. The suspension is centrifuged at 1000 rpm for 60 minutes, the supernatant is taken up in 50 ml of water for injection purposes. The centrifuging against water for injection purposes is repeated another 4 times. The supernatant of the final centrifuging is taken up with 50 ml of water for injection purposes and filtered through a filter column from HDC-pore filters of pore sizes 70, 40, 20 and 10 $\mu$m. The filtrate contains about $2 \times 10^9$ particles/ml, which have DTPA groups on their surface. The average particle size is about 2 $\mu$m. The particles can be labeled with the known methods with radioactive metal ions (e.g., In-111 or Tc-99).

EXAMPLE 21

Fibrin clots as examples for sound application lead to detection only with a gamma counter instead of with Doppler.

EXAMPLE 22

7.5 g of polygeline is dissolved at 80° C. in 150 ml of water for injection purposes. After cooling, the solution is adjusted to pH 3 with 0.1 N HCl and supplemented with water for injection purposes to 300 ml. The solution is autoclaved (process A 121, German Pharmacopoeia 9 th Edition). The pH of the autoclaved solution is corrected to pH 2. 3 ml of cyanoacrylic acid butyl ester is added to the solution with stirring. Stirring is continued for 90 minutes. The resulting microparticle suspension is centrifuged at 1000 rpm for 60 minutes, the supernatant is taken up in 50 ml of water for injection purposes and again centrifuged at 1000 rpm for 60 minutes. This is repeated a total of 5 times. The supernatant of the final centrifuging is taken up in 50 ml of PBS (pH 7.4) and cooled to 4° C. With stirring at 4° C., 50 mg of streptavidin and 5 mg of EDC are added. Stirring is continued for 1 hour. The suspension is centrifuged 3 times (1000 rpm, 60 minutes). After each centrifuging, the supernatant is taken up with 50 ml of PBS (pH 7.0, 10 mmol of phosphate). The antibody against fibrin is labeled in a molar ratio of 1:5 with sulfosuccinimidyl-6-(biotinamido)-hexanoate (NHS-LC-biotin) according to the method of D. J. Hnatovitch et al., J. Nucl. Med. 28 (1987), 1294–1302.

EXAMPLE 23

0.5 mg of the biotin-labeled antibody against fibrin of example 22 is intravenously injected in a rabbit fed with a diet containing cholesterol. After 3 hours, the particles of example 22 are then injected. 10 minutes later, the carotid is removed from the previously killed animal, and the atherosclerotic arterial sections are examined in a water bath in the Doppler mode for contrast media signals. Sound signals of clinging particles can clearly be detected.

EXAMPLE 24 a) 20 ml of the microparticle suspension produced according to example 8 is brought to a pH of 4.5 by 5 ml of phosphate buffer and then mixed with 50 mg of a 125-iodine labeled antibody against fibrin (5 $\mu$Ci). With stirring at 4° C., 500 mg of (3 -dimethylaminopropyl)-N'-ethylcarbodiimide hydrochloride is added to the reaction mixture. Then, stirring is continued for 8 hours under cooling, the microparticles are separated by centrifuging and washed a total of three times with 20 ml each of water for injection purposes, and each individual washing process takes place in the way that the particles are resuspended in water and then centrifuged. After the final washing process, the particles are resuspended in 20 ml of water for injection purposes.

The degree of bonding of the antibody to the particle is determined with a gamma counter based on the 125-iodine activity. Then, 93% of the originally used amount of antibodies is bound permanently to the particle surface.

b) Microparticles produced according to example 4 of DE 38 03 972 are reacted in an amount corresponding to example 24a) with 50 mg of a 125-iodine labeled antibody against fibrin (5 $\mu$Ci) under otherwise identical reaction conditions.

A comparison of the degree of bonding with the particles according to example 24a) shows a considerably lower value of only 1%.

What is claimed is:

1. Microcapsules having a core defined by a wall material comprising a copolymer of at least one synthetic polymeric material and at least one biopolymer, wherein
   a) the biopolymer exhibits site-specific, structure-specific or tissue-specific properties or
   b) the biopolymer has functional groups, by which, optionally, chelating ligands or their metal complexes and/or site specific, structure-specific or tissue-specific substances are bound,
   c) the synthetic polymeric material has a hydrophobic alkylbackbone, and
   d) optionally, the wall material contains one or more pharmaceutically active ingredient(s)
and wherein the core of the microcapsules comprises
   a) a gas or gas mixture,
   b) one or more pharmaceutically active ingredients or
   c) the same material as the capsule wall,
      provided that the synthetic polymeric material is not made of polymerizable aldehydes, and
      wherein the weight ratio of biopolymer to synthetic polymeric material is in the range of 10:90 to 80:20 and
      wherein the microcapsule size is 0.5 to 8 $\mu$m.

2. Microcapsules according to claim 1, wherein the synthetic polymeric material comprises monomeric acrylic acid, acrylamide, acrylic acid chloride, acrylic acid glycide ester or monomeric alkylcyanoacrylates.

3. Microcapsules according to claim 1, wherein the biopolymer is an optionally glycosylated polypeptide.

4. Microcapsules according to claim 1, wherein the site-specific, structure-specific and tissue-specific substances optionally bound by the functional groups of the biopolymer are antibodies, conjugated antibodies, hormones, transferrin, fibronectin, heparin, transcobalamin, epidermal growth factor, lipoproteins, plasma proteins, peptides or oligopeptides.

5. Microcapsules according to claim 1, wherein the biopolymer is a polypeptide with site-specific, structure-specific and tissue-specific properties.

6. Microcapsules according to claim 1, wherein the wall material encloses a gas.

7. Microcapsules according to claim 1, wherein chelating ligands are bound by the functional groups of the biopolymer.

8. Microcapsules according to the claim 7 containing ethylenediaminepentaacetic acid radicals or their derivatives as chelating agents.

9. Microcapsules according to claim 1, wherein chelate complexes of metal ions are bound by the functional groups of the biopolymer are chelate complexes of metal ions.

10. Microcapsules according to claim 9, wherein the metal ions are paramagnetic.

11. Microcapsules according to claim 10, wherein the metal ions are gadolinium ions.

12. Microcapsules according to claim 9, wherein the metal ions are radioisotopes.

13. Microcapsules according to claim 12, wherein the radioisotopes are $^{99m}$technetium ions or $^{111}$indium ions.

14. A process for the production of microcapsules according to claim 1, comprising (1) polymerizing at least one monomer dispersed in a production solution to obtain microcapsules, wherein the production solution comprises
   a gas-saturated, optionally autoclaved aqueous phase,
   0.01–10% (m/v) of at least one monomer, relative to the total volume of the production solution with dispersion
   a dissolved biopolymer in a concentration of 0.5–20% (m/v),
   optionally, magnetic particles,
provided that the weight ratio of biopolymer to synthetic polymer is 10:90 to 80:20, (2) after said polymerization, separating the microcapsules according to density and particle size by one-time or repeated centrifugation, filtration, sedimentation or flotation, (3) optionally further purifying the microcapsules by dialysis and (4) suspending the separated or purified microcapsules in a physiologically compatible suspending agent and (5) then optionally reacting the suspended microparticles with chelating agents, metal chelates and/or site-specific, structure-specific or tissue-specific substances.

15. Contrast medium comprising microparticles according to claim 1 suspended in a pharmaceutically acceptable suspension medium.

16. Contrast medium according to claim 15, wherein the pharmaceutically acceptable suspension medium comprises water, which optionally contains common salt, glucose, mannitol, or a multivalent alcohol.

17. A process for the production of microcapsules according to claim 14, further comprising freeze-drying the microcapsules.

18. Microcapsules according to claim 4, wherein the peptides or oligopeptides contain the amino acid sequences RGD, RGDS, RGDV or RGDT.

19. Microcapsules according to claim 6, wherein the gas is air, nitrogen, carbon dioxide, oxygen, helium, neon, argon, krypton or a mixture of at least two of these gases.

20. A process according to claim 14, wherein the production solution comprises
   0.1–10% (m/v) of said at least one monomer and 0.5–20% (m/v) of said dissolved polymer.

21. Microcapsules according to claim 3, wherein the glycosylated polypeptide is albumin, fibrinogen, fibronectin, a collagen decomposition product, gelatin, polygeline, oxypolygelatin or poly-L-lysine.

* * * * *